United States Patent [19]
Rutsch et al.

[11] Patent Number: 5,147,901
[45] Date of Patent: Sep. 15, 1992

[54] PROPIONPHENONE DERIVATIVES AS PHOTOINITIATORS FOR PHOTOPOLYMERIZATION

[75] Inventors: Werner Rutsch, Fribourg; Rudolf Kirchmayr, Aesch; Rinaldo Hüsler, Basel; Kurt Dietliker, Fribourg, all of Switzerland

[73] Assignee: Ciba-Geigy Corporation, Ardsley, N.Y.

[21] Appl. No.: 411,436

[22] Filed: Sep. 22, 1989

Related U.S. Application Data

[60] Division of Ser. No. 245,088, Sep. 16, 1988, abandoned, which is a division of Ser. No. 880,654, Jun. 30, 1986, Pat. No. 4,795,766, which is a continuation of Ser. No. 756,912, Jul. 17, 1985, abandoned, which is a continuation of Ser. No. 534,954, Sep. 22, 1983, abandoned.

[30] Foreign Application Priority Data

Oct. 1, 1982 [CH] Switzerland ............... 5807/82

[51] Int. Cl.$^5$ .................. C08F 2/50; C08F 4/72; C08F 20/20
[52] U.S. Cl. ................. 522/42; 522/103; 522/182
[58] Field of Search ................. 522/42, 41

[56] References Cited

U.S. PATENT DOCUMENTS

| | | | |
|---|---|---|---|
| 3,636,026 | 1/1972 | Fuhr | 522/43 |
| 3,657,088 | 4/1972 | Heine | 522/42 |
| 3,689,565 | 9/1972 | Hoffmann | 522/40 |
| 4,141,806 | 2/1979 | Keggenhoff | 522/42 |
| 4,318,791 | 3/1982 | Felder et al. | 522/44 |

FOREIGN PATENT DOCUMENTS 2357866 6/1974 Fed. Rep. of Germany .

Primary Examiner—Marion E. McCamish
Assistant Examiner—Arthur H. Koeckert
Attorney, Agent, or Firm—Luther A. R. Hall

[57] ABSTRACT

Propiophenones of the formula I

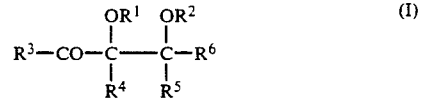

in which $R^1$ is hydrogen or $C_1$–$C_4$-alkyl, —Si(CH$_3$)$_3$, allyl or benzyl, $R^2$ is hydrogen, $C_1$–$C_8$-alkyl, $C_1$–$C_4$-alkyl which is substituted by $C_1$–$C_4$-alkoxy or —OH, —(CH$_2$—CH$_2$—O)$_n$—$R^5$ where n is 2 to 20 and $R^5$ is H or $C_1$–$C_4$-alkyl, —Si(CH$_3$)$_3$, benzyl, $C_3$–$C_6$-alkenyl, $C_3$–$C_4$-alkynyl or 2-tetrahydrofuranyl, or $R^1$ and $R^2$ together are a $C_1$–$C_6$-alkylidene radical or a $C_2$–$C_6$-alkylidene radical which is substituted by hydroxyl, $C_1$–$C_4$-alkoxy or phenyl, a linear or branched $C_2$–$C_6$-alkanediyl radical, a benzylidene, cyclopentylidene or cyclohexylidene radical or a 2,2,2-trichloroethylidene, 2-furylmethylidene or dimethylsilylidene radical, $R^3$ is phenyl which is unsubstituted or substituted by one or more —Cl, $C_1$–$C_4$-alkyl, $C_1$–$C_4$-alkoxy or $C_1$–$C_4$-alkylthio radicals, and is also benzoylphenyl, phenoxyphenol or phenylthiophenyl, $R^4$ is $C_1$–$C_4$-alkyl, or phenyl which is unsubstituted or substituted by one or more —Cl, $C_1$–$C_4$-alkyl or $C_1$–$C_4$-alkoxy radicals, and $R^5$ is hydrogen or $C_1$–$C_4$-alkyl, or $R^4$ and $R^5$ together are a trimethylene or tetramethylene radical, and $R^6$ is hydrogen, $C_1$–$C_4$-alkyl, —CCl$_3$ or phenyl, subject to the condition that, if $R^2$, $R^5$ and $R^6$ at the same time are hydrogen and $R^3$ and $R^4$ are at the same time phenyl, $R^1$ must not be hydrogen or $C_1$–$C_4$-alkyl, also, if $R^3$ and $R^4$ at the same time are phenyl and $R^5$ and $R^6$ are at the same time hydrogen, $R^1$ and $R^2$ together must not be alkylidene or benzylidene, and also, if $R^3$ and $R^4$ at the same time are p-methoxyphenyl and $R^2$, $R^5$ and $R^6$ are at the same time hydrogen, $R^1$ must not be hydrogen, and, finally, if $R^2$ and $R^6$ at the same time are hydrogen and $R^3$, $R^4$ and $R^5$ are at the same time phenyl, $R^1$ must not be hydrogen, are valuable initiators for the photopolymerization of ethylenically unsaturated compounds.

8 Claims, No Drawings

PROPIONPHENONE DERIVATIVES AS PHOTOINITIATORS FOR PHOTOPOLYMERIZATION

This is a divisional of application Ser. No. 245,088, filed Sep. 16, 1988, now abandoned; which is a divisional of application Ser. No. 880,654, filed Jun. 30, 1986, now U.S. Pat. No. 4,795,766, issued Jan. 3, 1989; which is a continuation of application Ser. No. 756,912, filed Jul. 17, 1985, now abandoned; which is a continuation of application Ser. No. 534,954, filed Sep. 22, 1983, now abandoned.

The invention relates to the use of selected aromaticaliphatic ketones as initiators for the photopolymerisation of ethylenically unsaturated compounds or the photochemical crosslinking of polyolefines, and to the photopolymerisable or crosslinkable systems containing initiators of this type.

Photochemical polymerisation processes have acquired considerable importance in industry, particularly in cases where thin films have to be cured within a short time, for example when curing lacquer coatings or when drying printing inks. Compared with conventional curing processes, UV irradiation in the presence of photoinitiators has a number of advantages, of which perhaps the most important is the high rate of photocuring. The rate depends greatly on the photoinitiator used, and there has been no lack of attempts to replace the conventional initiators by increasingly better and more effective compounds.

Amongst the most important photoinitiators are derivatives of aromatic-aliphatic ketones, particularly propiophenone derivatives such as are described, for example, in U.S. Pat. Nos. 4,318,791, 4,072,694 and in German Offenlegungsschrift 2,357,866.

However, the properties of compounds of this type are still not optimal, particularly in respect of stability on storage, reactivity and tendency to yellowing.

There is, therefore, a need in industry for photoinitiators which are readily soluble in the substrate and initiate photopolymerisation more rapidly, while having good stability when stored in the dark, and which produce an even higher polymer yield per time unit than the known photoinitiators. The use of such improved photoinitiators would enable the expensive industrial UV irradiation equipment to be utilised better.

It has been found that certain aromatic-aliphatic propiophenones possess excellent properties as photoinitiators and thereby improve the photopolymerisation of ethylenically unsaturated compounds. The invention relates to photopolymerisable compositions comprising at least one ethylenically unsaturated photopolymerisable compound and an effective quantity of a propiophenone derivative of the formula I

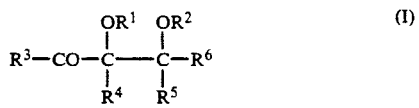

in which $R^1$ is hydrogen or $C_1$–$C_4$-alkyl, $-Si(CH_3)_3$, allyl or benzyl, $R^2$ is hydrogen, $C_1$–$C_8$-alkyl, $C_1$–$C_4$-alkyl which is substituted by $C_1$–$C_4$-alkoxy or $-OH$, $(CH_2-CH_2-O)_n$-$R^5$, where n is 2 to 20 and $R^5$ is H or $C_1$–$C_4$-alkyl, $-Si(CH_2-CH_2-O)_n$-$R^5$, benzyl, $C_3$–$C_6$-alkenyl, $C_3$–$C_4$-alkynyl, 2-tetrahydropyranyl or 2-tetrahydrofuranyl, or $R^1$ and $R^2$ together are a $C_1$–$C_6$ alkylidene radical or a $C_2$–$C_6$-alkylidene radical which is substituted by hydroxyl, $C_1$–$C_4$-alkoxy or phenyl, a linear or branched $C_2$–$C_6$-alkanediyl radical, a benzylidene, cyclopentylidene or cyclohexylidene radical or a 2,2,2-trichloroethylidene, 2-furylmethylidene or dimethylsilylidene radical, $R^3$ is phenyl which is unsubstituted or substituted, for example by one or more $-Cl$, $C_1$–$C_4$-alkyl, $C_1$–$C_4$-alkoxy or $C_1$–$C_4$alkylthio radicals, and is also benzoylphenyl, phen-oxyphenyl or phenylthiophenyl, $R^4$ is $C_1$–$C_4$-alkyl or phenyl which is unsubstituted or substituted by one or more $-Cl$, $C_1$–$C_4$alkyl, or $R^4$ and $R^5$ together are a trimethylene or tetramethylene radical, and $R^6$ is hydrogen, $C_1$–$C_4$-alkyl, $-CCl_3$ or phenyl, subject to the condition that, if $R^2$, $R^5$ and $R^6$ at the same time are hydrogen and if $R^3$ and $R^4$ are at the same time phenyl, $R^1$ must not be hydrogen or $C_1$–$C_4$-alkyl, and also, if $R^3$ and $R^4$ at the same time are phenyl and $R^5$ and $R^6$ are at the same time hydrogen, $R^1$ and $R^2$ together must not be alkylidene or benzylidene, and also, if $R^3$ and $R^4$ at the same time are p-methoxyphenyl and $R^2$, $R^5$ and $R^6$ are at the same time hydrogen, $R^1$ must not be hydrogen, and, finally, if $R^2$ and $R^6$ at the same time are hydrogen and $R^3$, $R^4$ and $R^5$ are at the same time $R^1$ must not be hydrogen. These compounds are initiators for the photopolymerisation of ethylenically unsaturated compounds and for the photochemical crosslinking of polyolefines.

$C_1$–$C_4$-alkyl radicals $R^1$, $R^2$, $R^4$, $R^5$ and $R^6$ are, for example, linear or branched alkyl groups, such as methyl, ethyl, n-propyl, isopropyl, n-butyl, sec.-butyl and tert.-butyl, but especially methyl.

$C_1$–$C_4$-alkyl substituents in phenyl as $R^3$ and $R^4$ are, for example, methyl, ethyl, n-propyl, isopropyl, n-butyl or tert.-butyl substituents.

$C_1$–$C_4$-alkoxy or $C_1$–$C_4$-alkylthio substituents in phenyl as $R^3$ are, for example, methoxy, ethoxy, propoxy or tert.-butoxy groups or methylthio, ethylthio, propylthio or tert.-butylthio substituents, respectively.

A $C_1$–$C_6$-alkylidene radical formed by $R^1$ and $R^2$ together is, for example, methylene, ethylidene, propylidene or especially isopropylidene, while a linear or branched $C_2$–$D_6$-alkadiyl radical formed by $R^1$ and $R^2$ together is, for example, ethanediyl or methylethanediyl.

A $C_2$–$C_6$-alkylidene radical substituted by hydroxyl which is formed by $R^1$ and $R^2$ together is, preferably, 1-hydroxy-2-propylidene, a$C_2$–$C_6$-alkylidene radical substituted by $C_1$–$C_4$-alkoxy which is formed by $R^1$ and $R^2$ together is, preferably, 1-methoxy-2-propylidene, while is formed by $R^1$ and $R^2$ together is, in particular, 1-phenyl1-ethylidene.

$C_1$–$C_4$-Alkoxy substituents in phenyl as $R^4$ are, for example, methoxy, ethoxy, propoxy or tert.-butoxy groups.

A $C_3$–$C_6$-alkenyl radical $R^2$ is, for example, prop2-enyl, n-but-2-enyl, 2-methylprop-2-enyl, n-pent-2-enyl or n-hex-2-enyl, while a $C_3$–$C_4$-alkinyl radical $R^2$ is, for example, prop-1-inyl or 3-buten-1-inyl.

$C_1$–$C_8$-Alkyl substituents in $R^2$ are, for example, linear or branched substituents, for example methyl, ethyl, n-propyl, isopropyl, n-butyl, sec.-butyl, tert.-butyl, pentyl, hexyl, heptyl or octyl.

All the position isomers are possible in the case of a $C_1$–$C_4$-alkyl radical $R^2$ which is substituted by $C_1$–$C_4$-alkoxy or $-OH$.

n is preferably 2 to 10 and $R^5$ is preferably methyl or ethyl in an $R^2$ radical which is substituted by —($CH_2$-$CH_2$-O)$_n$-$R^5$.

Preferred compounds of the formula I are those in which $R^1$ and $R^2$ are hydrogen, —Si($CH_3$)$_3$ or $C_1$-$C_4$-alkyl, especially methyl, $R^3$ is phenyl, $R^4$ is $C_1$-$C_4$-alkyl and $R^5$ is hydrogen, or in which $R^1$ and $R^2$ together are a trimethylene or tetramethylene radical and $R^6$ is hydrogen. Preferred compounds of the formula I are also those in which $R^1$ and $R^2$ together are a dimethylsilylidene radical.

Compounds of the formula I which are particularly preferred are those in which $R^1$, $R^5$ and $R^6$ are hydrogen, $R^2$ and $R^4$ are methyl and $R^3$ is phenyl, or, if $R^1$ is hydrogen, $R^2$ is methyl, $R^3$ is phenyl, $R^4$ and $R^5$ together are tetramethylene and $R^6$ is hydrogen, or in which $R^1$ and $R^2$ together are isopropylidene.

Compounds of the formula I which are particularly preferred are those in which $R^1$ is hydrogen, $R^2$ is hydrogen, methyl or —Si($CH_3$)$_3$, or $R^1$ and $R^2$ together are isopropylidene, benzylidene or dimethylsilylidene, $R^3$ is phenyl, $R^4$ is methyl or phenyl, $R^5$ is hydrogen, or $R^4$ and $R^5$ together are a tetramethylene radical and $R^6$ is hydrogen or phenyl, subject to the condition that $R^2$, $R^5$ and $R^6$ at the same time may not be hydrogen or $R^4$ may not be phenyl, and if $R^4$ is phenyl and $R^5$ and $R^6$ at the same time are hydrogen, $R^1$ and $R^2$ together may not be isopropylidene or benzylidene, and finally, $R^2$ may not be hydrogen and $R^4$ and $R^6$ at the same time may not be phenyl.

The following are examples of individual compounds of the formula I: 1-hydroxy-3-methoxy-2-methyl-1-phenylpropan-1-one, 3-benzyloxy-2-hydroxy-2-methyl-1-phenylpropan-1-one, 1,3-diphenyl-2-hydroxy-3-methoxy-2-methylpropan-1-one, 2-hydroxy-3-methoxy-2-methyl-1-phenyl-3-trichloromethylpropan-1-one, 1,2-diphenyl-2-hydroxy-3-methoxypropan-1-one, 3-allyloxy-1,2-diphenyl-2-hydroxypropan-1-one, 1,2-diphenyl2-hydroxy-3-trimethylsiloxypropan-1-one, 1,2-diphenyl-2-hydroxy-3-(2-tetrahydropyranyloxy)-propan-1-one, 2,3-dihydroxy-2-methyl-1-phenyl-3-trichloromethylpropan-1-one, 1-benzoyl-1-hydroxy-2-trimethylsilyloxycyclohexane, 1-benzoyl1-hydroxyl-2-methoxycyclohexane, 1-benzoyl-1,2-dihydroxycyclohexane, 4-benzoyl-5-trichloromethyl-2,2,4-trimethyl-1,3-dioxolane, 2,3-(dimethylsilylenedioxy)-1,2-diphenylpropan-1-one, 2,3-(dimethylsilylenedioxy)-2-methyl-1-phenylpropan-1-one, 2,3-(dimethylsilylenedioxy)-2-methyl-1-(4-methoxyphenyl)propan-1-one, 4-benzoyl-4-methyl-2-phenyl-1,3-dioxolane, 4-benzoyl-2,2,4-trimethyl-1,3-dioxolane, 4-(4-chlorobenzoyl)4-(4-chlorophenyl)-2-phenyl-1,3-dioxolane, 4-benzoyl-4,5-dimethyl-2-phenyl-1,3-dioxolane, 4-benzoyl-4-methyl-1,3-dioxolane, 4-benzoyl-4-methyl-2,2-pentamethylene-1,3-dioxolane, 4-benzoyl-2,2-pentamethylene-4-phenyl-1,3-dioxolane, 4-ethyl-4-benzoyl-2,2-tetramethylene-1,3-dioxolane, 4-ethyl4-(4-methoxybenzoyl)-2-propyl-1,3-dioxolane, 4-benzoyl-2,4-2-isopropyl-5-phenyl-1,3-dioxolane, 2-benzoyl-2-methyl-3-phenyl-1,4-dioxolane, 2-benzoyl-5-methyl-2-phenyl-1,4-dioxolane, 1,2-(dimethylsilylenedioxy)-1-benzoylcyclohexane, 1-benzoyl-8,8-dimethyl-7,9-dioxabicyclo[4.3.0]nonane, 1-benzoyl8,8-pentamethylene-7,9-dioxabicyclo[4.3.0]nonane, 2-hydroxy3-isopropoxy-2-methyl-1-phenyl-1-propan-1-one, 2-ethyl-3 -(2-ethylhexyl)oxy-2-hydroxy-1-(3-tolyl)-propan-1-one, 2hydroxy-3-(2-methoxyethyl)oxy-2-methyl-1-(4-methylthiophenyl3-phenylpropan-1-one, 2-ethyloxymethyl-2-hydroxy-1-(4-propoxyphenyl-hexan-1-one, 1-(4-benzoylphenyl)-2-hydroxy-2-methyl-3-(2-tetrahydrofuranyloxy)-propan-1-one, 1,2-diphenyl2-hydroxy-4,7,10-trioxaundecan-1-one, 2-hydroxy-1-(4-methoxy3-methylphenyl)-2-methyl-4,7,10-trioxadodecan-1-one, 1,2-diphenyl-2-hydroxy-4,7,10,13,16,19,22,25,28,31-decaoxatritriacontan-1-one, 1-(2-chloro-4-chloro-4-phenylthiophenyl)-2-ethyl-2-hydroxy-3-(2-propinyl)oxypropan-1-one, 1-(3,4-dimethylphenyl)3-butoxy-2-hydroxy-2-methyl-3-phenylpropan-1-one, 2,3-di-methyl-2-hydroxy-3-methoxy-1-phenylbutan-1-one, 3-(2-butenyl)oxy2-hydroxy-2-methyl-1-(2,4,6-trimethylphenyl)-propan-1-one, 1-(3,4-dimethoxyphenyl)-2-hydroxy-2-methoxymethylbutan-1-one, 1,2-diphenyl-2,3-bis(trimethylsiloxy)-propan-1-one, 1,2-bis(4-methoxyphenyl)-2,3-bis(allyloxy)-propan-1-one, 2,3-di-benzyloxy-2-methyl-1-(4-propylthiophenyl)-propan-1-one, 1-(4-tert.-butylphenyl)-2-ethyl-2,3-dimethoxy-3-phenylpropan1-one, 3-hydroxy-1,2-bis(4-methoxyphenyl)-2-trimethylsiloxypropan-1-one, 3-hydroxy-2-isopropyloxy-1,2,3-triphenylpropan-1-one, 2-allyloxy-1,2-diphenyl-3-hydroxypropan-1-one, 2-butyl-2-hydroxy-3-methoxy-4-methyl-1-(4-phenylthiophenyl)pentan-1-one, 2-hydroxy-2-methyl-1-(4-phenoxyphenyl)-3-trimethylsiloxypropan-1-one and 1-(4-chlorophenyl)-2-hydroxy3-(2-hydroxypropyl)oxy-2-methylpropan-1-one.

The compounds of the formula I are novel and are therefore also a subject of the present invention. Their preparation is effected analogously to that of the known compounds, for example in accordance with the relevant processes indicated in U.S. at. Nos. 4,318,791 and 4,072,694.

The following route of synthesis is particularly advantageous:

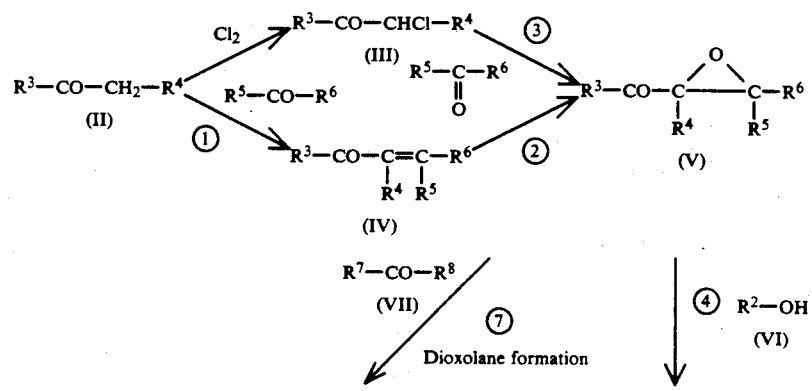

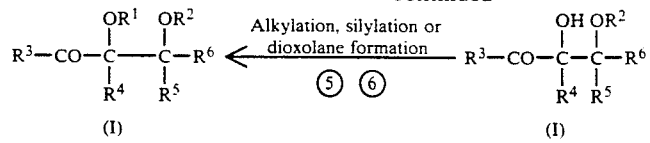

(I)    (I)

Starting from a propiophenone derivative of the formula II, the compound of the formula V is prepared either by means of $Cl_2$ via the chlorinated compound of the formula III or via the compound of the formula IV, and, after being reacted with an appropriate alcohol of the formula VI or with $H_2O$, is converted into the compound, according to the invention, of the formula I and, after further alkylation, silylation or dioxolane formation, is converted into the compound, according to the invention, of the formula I. Compounds of the formula I can also be formed direct from compounds of the formula V by dioxolane formation using a ketone or aldehyde of the formula VII. In this case, $R^7$ is hydrogen, $C_1$-$C_5$-alkyl or phenyl, $R^8$ is hydrogen or $C_1$-$C_2$-alkyl and $R^7$ and $R^8$ together are a tetramethylene or pentamethylene radical. In the formulae I, II, III, IV, V and VI, the radicals $R^1$ and $R^6$ are as defined above.

The numbers in circles indicate the literature references in which analogous processes of this type are described: ① J. Chem. Soc., 79, 928 (1901), ② J. Org. Chem., 28, 250, (1963) or Org. Syntheses, 55, 52 (1976), ③ J. Am Chem. Soc., 75, 2042 (1953), ④ J. Chem. Soc., 73, 3293 (1958) or Houben-Weyl, Methoden der organischen Chemie (Methods of Organic Chemistry), volume VI/3, 40-44, 456-457, (1965), ⑤ T. W. Greene, Protective Groups in Organic Synthesis, pages 40–42, (1981) or Houben-Weyl, Methoden der organischen Chemie (Methods of Organic Chemistry), volume VI/3, 229–232 (1963), ⑥ J. Am. Chem. Soc. 92, 5394 (1970), ⑦ Khim. Geterotsikl. Soedin 1975, 907.

Examples of such compounds are unsaturated monomers, such as esters of acrylic or methacrylic acid, for example methyl, ethyl, n-butyl, tert.-butyl, isooctyl or hydroxyethyl acrylate, methyl or ethyl methacrylate, ethylene diacrylate, neopentyl diacrylate, trimethylolpropane trisacrylate, pentaerythritol tetraacrylate or pentaerythritol trisacrylate; acrylonitrile, methacrylonitrile, acrylamide, methacrylamide or N-substituted (meth)acrylamides, vinyl esters, for example vinyl acetate, propionate, acrylate or succinate, other vinyl compounds, such as vinyl ethers, styrene, alkylstyrenes, halogenostyrenes, divinylbenzene, vinylnaphthalene, N-vinylpyrrolidone, vinyl chloride or vinylidene chloride; allyl compounds, such as diallyl phthalate, diallyl maleate, triallyl isocyanurate, triallyl phosphate or ethylene glycol diallyl ether, and mixtures of such unsaturated monomers.

Other photopolymerisable compounds are unsaturated oligomers or polymers and mixtures thereof with unsaturated monomers. These compounds include thermoplastic resins containing unsaturated groups, such as fumaric acid esters, allyl groups or acrylate or methacrylate groups. In most cases these unsaturated groups are linked to the main chain of these linear polymers via functional groups. Mixtures of oligomers with monounsaturated and polyunsaturated monomers are of great importance. Examples of such oligomers are unsaturated polyesters, unsaturated acrylic resins and isocyanate-modified or epoxide-modified acrylate oligomers and also polyether acrylate oligomers. Examples of polyunsaturated compounds are especially the acrylates of diols and polyols, for example hexamethylene diacrylate or pentaerythritol tetraacrylate. Acrylates, for example butyl acrylate, phenyl acrylate, benzyl acrylate, 2-ethylhexyl acrylate or 2-hydroxypropyl acrylate, are also preferred as monounsaturated monomers. By selecting the three components from the various representatives it is possible to vary the consistency of the unpolymerised mixture and also the plasticity of the polymerised resin.

As well as these three-component mixtures, two-component mixtures, in particular, play an important part in polyester resins. These mixtures consist in most cases of an unsaturated polyester and a vinyl compound. The unsaturated polyesters are oligomeric esterification products of at least one unsaturated dicarboxylic acid, for example maleic, fumaric or citraconic acid, and, in most cases, at least one saturated dicarboxylic acid, for example phthalic acid, succinic acid, sebacic acid or isophthalic acid, with glycols, for example ethylene glycol, 1,2-propanediol, diethylene glycol, triethylene glycol or tetramethylene glycol, monocarboxylic acids and monoalcohols also being used concomitantly for modification in most cases. These unsaturated polyesters are usually dissolved in a vinyl or allyl compounds, styrene being preferably used for this purpose.

Preferred ethylenically unsaturated photopolymerisable compounds are monofunctional, bifunctional or polyfunctional acrylic esters and/or methacrylic esters or mixtures thereof.

Many of the compounds employed in the practice of this invention are also suitable for use as initiators in aqueous photopolymerisable and curable systems. Examples of aqueous dispersions are described in the following publications: EP 12339, EP 21078, EP 41125, DE-OS 2 936 039 and DE-OS 3 005 036.

Photopolymerisable systems such as are used for various purposes in most cases contain a number of other additives besides the photopolymerisable compounds and the photoinitiator. Thus it is often customary to add thermal inhibitors which are intended to protect the systems from premature polymerisation, especially while the systems are being prepared by mixing the components. Examples of compounds used for this purpose are hydroquinone, hydroquinone derivatives, p-methoxyphenol, β-naphthylamine or β-naphthols. It is also possible to add small quantities of UV absorbers, for example those of the benzotriazole or benzophenone type.

Stability to storage in the dark can be increased by adding copper compounds, such as copper naphthenate, stearate or octoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzylammonium chloride or hydroxylamine derivatives, for example N-diethylhydroxylamine. The photopolymerisable systems can also contain chain transfer agents, for example N-methyldiethanolamine, triethanolamine or cyclohexane.

In order to exclude the inhibiting action of the oxygen of the air, paraffin or similar waxlike substances are frequently added to photocurable systems. These float to the top at the start of polymerisation owing to inadequate solubility in the polymer, and form a transparent surface layer which prevents the access of air. It is also possible to deactivate the oxygen of the air by introducing autooxidisable groups, for example allyl groups, into the resin to be cured.

The photoinitiators can also be used in combination with free radical initiators, for example peroxides, hydroperoxides, ketone peroxides or percarboxylic acid esters.

Depending on their end use, photopolymerisable systems also contain fillers, such as silica, talc or gypsum, pigments, dyes, fibres, thixotropic agents or flow control auxiliaries.

It is also possible to use combinations containing known photoinitiators, such as benzoin ethers, dialkoxyacetophenone or benzil ketals.

Combinations of the photoinitiators according to the invention with amines and/or aromatic ketones can be used, in particular, for the photopolymerisation of thin layers and printing inks. Examples of amines are triethylamine, N-methyldiethanolamine, N-dimethylethanolamine or p-dimethylaminobenzoic acid esters. Examples of ketones are benzophenone, substituted benzophenone derivatives, Michler's ketone, anthraquinone and anthraquinone derivatives, coumarin derivatives and thioxanthone and derivatives thereof.

The photocuring of printing inks is of great importance, since the drying time of the binder is a decisive factor for the rate of production of graphic products and should have an order of magnitude of fractions of a second. The initiators according to the invention are also very suitable for photocurable systems for the production of printing plate. Mixtures of soluble linear polyamides with photopolymerisable monomers, for example, used in this case. Films and plates belonging to these systems are exposed via the negative (or positive) of the print original, and the uncured portions are then eluted by means of a solvent.

A further field of use for UV curing is metal coating, for example in the lacquering of metal sheets for tubes, cans or bottle closures, and also the UV curing of plastic coatings, for example floor coverings or wall coverings based on PVC.

Examples of the UV curing of paper coatings are the colourless lacquering of labels, gramophone record sleeves or book covers.

The compounds of the formula I can also be used in accordance with the invention as initiators for the photochemical crosslinking of polyolefines. Examples of polyolefines suitable for this purpose are polypropylene, polybutylene, polyisobutylene and copolymers, for example ethylene/propylene copolymers, but preferably low-density, mediumdensity or high-density polyethylene.

For the fields of use mentioned, it is advantageous to use the photoinitiators in amounts of 0.1 to 20% by weight, preferably about 0.5 to 5% by weight, based on the photopolymerisable or crosslinkable composition. Composition is to be understood in this context as meaning the mixture of the photopolymerisable or crosslinkable compound, the photoinitiator and the other fillers and and additives, as used in the particular application.

The addition of the photoinitiators to the photopolymerisable compositions is generally effected merely by stirring in, since most of these compositions are liquid or readily soluble. In most cases a solution of the initiators according to the invention is used, which ensures uniform distribution of the latter and also transparency of the polymers.

The polymerisation is effected in accordance with known methods of photopolymerisation by irradiation with light rich in short-wave radiation. Examples of suitable light sources are medium-pressure, high-pressure and lowpressure mercury vapour lamps, and also superactinic fluorescent tubes having emission maxima in the range between 250 and 400 nm.

The propiophenones of the formula I according to the invention possess an improved reactivity and stability on storage and also an increased resistance to yellowing.

The preparation and use of the photoinitiators according to the invention is described in greater detail in the examples which follow. In these examples, parts and percentages are by weight.

EXAMPLE 1

Preparation of
3-methoxy-2-hydroxy-2-methyl-1-phenylpropan-1-one 20 parts (0.12 mol) of the educt, 2-benzoyl-2-methyloxirane of the formula

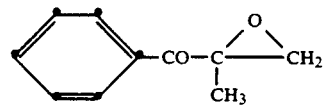

[prepared from α-chloropropiophenone and paraformaldehyde by means of $KOC(CH_3)_3/HOC(CH_3)_3$ analogously to the literature reference J. Am. Chem. Soc. 75, 2042 (1953)], are taken up in 50 ml of methanol, and a catalytic amount (approx. 5–10 mol %) of an acid, such as p-toluenesulfonic acid, is added carefully. The mixture is then stirred at room temperature until the educt is no longer present. The reaction solution thus obtained is then diluted with 250 ml of ether, washed twice with water, dried over sodium sulfate and finally concentrated on a rotary evaporator at 40° C. The crude reaction product obtained is purified by column chromatography (carrier: silica gel; mobile phase: hexane +20% by volume of ethyl acetate). This gives 12 parts of a pure, colourless, oily product of the formula

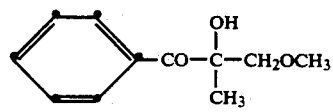

Analytical data: Combustion analysis for $C_{11}H_{14}O_3$: Calculated C % 68.03 H % 7.27; Found C % 68.04 H % 7.42.

NMR spectrum [$CDCl_3$, δ (in ppm)]: 1.43 (S,3H); 3.22 (S,3H); 3.38 and 3.84 (AB system, J=9Hz, 2H); 4.18 (S,1H); 7.1–7.4 (M,3H); 7.8–8.05 (M,2H).

S is singlet and M is multiplet.

Further compounds of the formula I were prepared analogously to the above example. They are listed in Table 1 below.

TABLE 1

| Example | Structure of the compounds of the formula I | Melting point (°C.) |
|---|---|---|
| 2 | Ph-C(=O)-C(OH)(—)–(ring with OH) [benzoyl with dioxolane-type OH,OH] | 82–84 |
| 3 | Ph-C(=O)-C(OH)(—)–(ring with OCH₃) | 85–87 |
| 4 | Ph-C(=O)-C(OH)(CH₃)-CH₂O-CH₂-Ph | (oil) |
| 5 | Ph-C(=O)-C(OH)(CH₃)-CH(OCH₃)-Ph | (oil) |
| 6* | Ph-C(=O)-C(OH)(—)–(ring with OSi(CH₃)₃) | 58–59 |
| 7* | Ph-C(=O)-C(OH)(Ph)-CH₂-OSi(CH₃)₃ | 76–77 |
| 8 | Ph-C(=O)-C(CH₃)(—O—)-CH₂(—O—)-C(CH₃)(CH₃) [4-benzoyl-2,2,4-trimethyl-1,3-dioxolane] | (Oel) |
| 9 | Ph-C(=O)-C(CH₃)(—O—)-CH₂(—O—)-CH(H)(Ph) [4-benzoyl-4-methyl-2-phenyl-1,3-dioxolane] | (Oel) |

*prepared by silylating the corresponding alcohols by means of Cl—Si(CH₃)₃ and N(C₂H₅)₃, in CH₂Cl₂.

EXAMPLE 8

Preparation of 4-benzoyl-2,2,4-trimethyl-1,3-dioxolane 16.2 g (0.1 mol) of 2-benzoyl-2-methyloxirane (see Example 1) are dissolved in 35 g (0.6 mol) of acetone, and a solution of 1.42 g (0.01 mol) of boron trifluoride-etherate in 35 g (0.6 mol) of acetone is then added dropwise while the mixture is cooled by means of an ice bath. The mixture is then stirred for 2 hours at room temperature and is then heated under reflux for 5 hours. The reaction solution is cooled, rendered alkaline, with cooling, by means of 50 ml of saturated methanolic sodium hydroxide solution, and diluted with 200 ml of water. The product is extracted with ether. The ether solution is dried with potassium carbonate and concentrated. The residue is distilled in vacuo at 95° C. and 0.5° mbar. The distillate is purified by mediumpressure chromatography, a colourless oil being obtained.

Analytical data: Combustion analysis for $C_{13}H_{16}O_3$ Calculated: C % 70.89 H % 7.33; Found: C % 70.76 H % 7.31.

¹H-NMR spectrum [CDCL₃, δ (in ppm)]: 8.25–7.95 (M, 2H); 7.45–7.2 (M, 3H); 4.64 and 3.70 (AB system, J=16 Hz, 2H); 1.57 (S,3H); 1.43 (S,3H); 1.10 (S,3H), S being singlet and M being multiplet.

EXAMPLE 9

Preparation of 4-benzoyl-4-methyl-2-phenyl-1,3-dioxolane

4-Benzoyl-4-methyl-2-phenyl-1,3-dioxolane was also prepared using benzaldehyde analogously to the above Example 8 (an oil having a boiling point of 145° C. at 0.07 mbar).

Analytical data: Combustion analysis for $C_{17}H_{16}O_3$: Calculated: C % 76.10 H % 6.01; Found: C % 76.11 H % 6.02.

¹H-NMR spectrum [CDCl₃, δ (ppm)]: 8.25–7.85 (M, 2 aromatic H); 7.5–6.9 (M, 8 aromatic H); 5.95 (S, 0.5 H,H—C(2)); 5.62 (S, 0.5 H,H—C(2)); 4.85 and 3.69 (1.0 H, signals of an AB system, J=8 Hz, 2H-C(5)); 4.55 and 3.85 (1.0 H, signals of an AB system, J=8 Hz, 2H-C(5)); 1.63 (S, CH₃-C(4)); 1.60 (S, CH₃-C(4)). The presence of a mixture of cis-trans-isomers (44% and 56%) if 4-benzoyl4-methyl-2-phenyl-1,3-dioxolane is deduced from the ¹H-NMR spectrum and the gas chromatogram.

USE EXAMPLES

EXAMPLE 10

A resin mixture composed of 20 parts of Plex ® 6616 (an acrylic resin made by Röhm, Darmstadt), 5 parts of trimethylolpropane trisacrylate and 0.5 part of 3-methoxy2-hydroxy-2-methyl-1-phenylpropan-1-one is applied to a sheet of glass in a thickness of 40 μm dry layer thickness by means of a film applicator. This film is exposed to the air for approx. 20 seconds and is then irradiated with a UV apparatus (PPG-QC-processor model). The sample is then passed under the UV lamp on a conveyor belt at a speed of 17 ml/minute. The film is resistant to wiping after 3 passes. The pendulum hardness (DIN 53,158) of the film cured in this way is 176 seconds.

EXAMPLE 11

A resin mixture composed of 80 parts of Plex ® 6616 (acrylic resin made by Röhm, Darmstadt), 20 parts of trimethylolpropane trisacrylate and 2 parts of photoinitiator is applied to sheets of glass in a thickness of 40 μm dry layer thickness by means of a film applicator. These films are exposed to the air for approx. 20 seconds and are then irradiated with a medium-pressure Hg lamp (Hanovia-Gerät, model 45,080). The samples are then passed under the UV lamp on a conveyor belt at a speed such that an effective exposure time of 0.16 second per pass results.

The number of passes (P) required to give tack-free films (resistant to wiping) is given in the second column of Table 2 below.

The third column gives the hardness of the films after the number of passes stated, measured with the Konig pendulum apparatus. Discolouration (yellowing) is assessed by determining the yellowness index as specified in ASTM D 1925-70.

TABLE 2

| Photoinitiator according to Example | Passes required (P) | König pendulum hardness when resistant to wiping (seconds) | Yellowness index |
|---|---|---|---|
| 1 | 3 | 176 | 4 |
| 2 | 3 | 115 | 4 |
| 3 | 3 | 162 | 4 |
| 4 | 3 | 184 | 5 |
| 5 | 5 | 179 | 4 |

EXAMPLE 12

A resin mixture composed of 80 parts of Ebecry ® 593 (acrylic resin made by UCB, Brussels), 20 parts of DQM672 (acrylic monomer made by Rohm and Haas, Philadelphia, USA) and 2 parts of photoinitiator is applied to sheets of glass in a thickness of 40 μm dry layer thickness by means of a film applicator. These films are exposed to the air for approx. 20 seconds and then irradiated with a medium-pressure Hg lamp (Hanovia-Gerät, model 45,080). This is effected by passing the samples under the UV lamp on a conveyor belt at a speed such that an effective exposure time of 0.16 second per pass results.

The number of passes (P) required to produce tack-free films (resistant to wiping) is given in the second column of Table 3 below.

The third column gives the hardness of the films after the number of passes stated, measured with the Konig pendulum apparatus. Discolouration (yellowing) is assessed by determining the yellowness index as specified in ASTM D 1925-70.

TABLE 3

| Photoinitiator according to Example | Passes required (P) | König pendulum hardness when resistant to wiping (seconds) | Yellowness index |
|---|---|---|---|
| 5 | 4 | 129 | 6 |
| 6 | 3 | 113 | 8 |
| 7 | 2 | 71 | 8 |

EXAMPLE 13

A resin mixture composed of 50 parts of Actylan ® AJ20 (acrylic resin made by SNPE, Paris Cedex), 15 parts of DQM-672 (acrylic monomer made by Rohm and Haas, Philadelphia, USA), 15 parts each of trismethylolpropane triacrylate and hexanediol diacrylate (polyfunctional monomers made by Degussa, Frankfurt), 10 parts of N-vinylpyrrolidone (reactive thinner made by GAF, New York, USA) and 2 parts of photoinitiator is applied to sheets of glass in a thickness of 40 μm dry layer thickness by means of a film applicator. These films are exposed to the air for approx. 20 seconds and are then irradiated with a high-pressure Hg lamp (UV-processor model 1202 AN made by PPG Radiation Polymer Company, USA). This is effected by passing the samples under the UV lamp on a conveyor belt at a belt speed such that an effective exposure time of 1.05 seconds per pass results.

The number of passes (P) required to give tack-free films (resistant to wiping) is given in the second column of Table 4 below.

The third column gives the hardness of the films after the number of passes stated, measured by the König pendulum apparatus.

The discolouration (yellowing) is assessed by determining the yellowness index as specified in ASTM D 1925-70.

TABLE 4

| Photoinitiator according to Example | Passes required (P) | König pendulum hardness when resistant to wiping (seconds) | Yellowness index |
|---|---|---|---|
| 1 | 8 | 151 | 8 |
| 3 | 9 | 158 | 8 |
| 4 | 10 | 163 | 7 |
| 6 | 10 | 161 | 7 |
| 7 | 7 | 148 | 9 |
| 8 | 6 | 153 | 10 |
| 9 | 7 | 147 | 8 |

What is claimed is:

1. A photopolymerizable composition comprising
   (a) at least one ethylenically unsaturated photopolymerizable compound, and
   (b) a compound of formula I

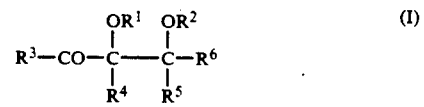

in which $R^1$ is hydrogen, $R^2$ is $-Si(CH_3)_3$, $R^3$ is phenyl, or said phenyl substituted by one or more $-Cl$, $C_1-C_4$-alkyl, $C_1-C_4$-alkoxy or $C_1-C_4$-alkylthio; or $R^3$ is benzoylphenyl, phenoxyphenyl or phenylthiophenyl, $R^4$ is $C_1-C_4$-alkyl, phenyl or phenyl substituted by one or more $-Cl$, $C_1-C_4$-alkyl or $C_1-C_4$-alkoxy, $R^5$ is hydrogen or $C_1-C_4$-alkyl, or $R^4$ and $R^5$ together are trimethylene or tetramethylene, and $R^6$ is hydrogen, $C_1-C_4$-alkyl, $-CCl_3$ or phenyl.

2. A composition according to claim 1 where in the compound of the formula I $R^3$ is phenyl, $R^4$ is $C_1-C_4$-alkyl and $R^5$ is hydrogen, or $R^4$ and $R^5$ together are a trimethylene or tetramethylene radical and $R^6$ is hydrogen.

3. A composition according to claim 1 where in the compound of the formula I $R^1$, $R^5$ and $R^6$ are hydrogen, $R^4$ is methyl and $R^3$ is phenyl.

4. A composition according to claim 1 where in the compound of the formula I $R^1$ and $R^6$ are hydrogen, $R^3$ is phenyl and $R^4$ and $R^5$ together are tetramethylene.

5. A composition to claim 1, comprising, as the ethylenically unsaturated photopolymerisable compound, a monofunctional, bifunctional or polyfunctional acrylic acid ester or methacrylic acid ester or mixtures thereof.

6. A printing ink comprising a photopolymerisable composition according to claim 1.

7. Metal, plastics and paper coatings comprising a photopolymerisable composition according to claim 1.

8. A composition according to claim 1 where in the compound of formula I, $R^1$, $R^5$ and $R^6$ are hydrogen; and $R^3$ and $R^4$ are phenyl.

* * * * *